United States Patent [19]

Andersson et al.

[11] 4,191,359

[45] Mar. 4, 1980

[54] CONTROL APPARATUS FOR CONTROLLING POSITIONING OF A CONTROL MEMBER

[75] Inventors: Roland J. E. Andersson, Bjarred; Lars-Ake L. Larsson, Loddenkopinge; Lars J. C. Traven, Lund, all of Sweden

[73] Assignee: Gambro AB, Sweden

[21] Appl. No.: 857,285

[22] Filed: Dec. 5, 1977

[30] Foreign Application Priority Data

Dec. 3, 1976 [SE] Sweden .................................. 7613576

[51] Int. Cl.$^2$ .............................................. F16K 7/06
[52] U.S. Cl. ........................................ 251/9; 251/129; 251/133; 251/205; 269/237; 269/241
[58] Field of Search ........................................ 251/4–10, 251/129, 130, 242, 243, 289, 205; 269/157, 237, 240, 241; 128/346

[56] References Cited

U.S. PATENT DOCUMENTS

| 1,466,704 | 9/1923 | DuPont | 251/289 X |
| 2,618,270 | 11/1952 | Pearson | 251/9 X |
| 2,791,239 | 5/1957 | Mason | 251/9 X |
| 2,827,257 | 3/1958 | Becker et al. | 251/9 |
| 3,012,701 | 12/1961 | Weber | 251/7 X |
| 3,203,421 | 8/1965 | Bialick | 251/9 X |

FOREIGN PATENT DOCUMENTS

| 78050 | 8/1954 | Denmark | 251/7 |
| 414952 | 12/1966 | Switzerland | |
| 432730 | 9/1967 | Switzerland | |

*Primary Examiner*—Martin P. Schwadron
*Assistant Examiner*—Richard Gerard
*Attorney, Agent, or Firm*—Lerner, David, Littenberg & Samuel

[57] ABSTRACT

Control apparatus for controlling or adjusting the position of a control member is disclosed. The control apparatus includes first and second members, pivotally connected together to pivot about a point. A control member is mounted on the first member and is disposed at a first distance from the pivot point. Coarse control means operatively associated with the control member are provided for coarsely adjusting the position of the control member relative to the second member. Further, fine control means are provided for finely adjusting the position of the control member relative to the second member. The fine control means acts at an action point on one of the first and second members to pivot the first and second members relative to each other about the pivot point. The action point at which the fine control means acts is a second distance from the pivot point which is greater than the first distance such that a selected amount of movement of the action point results in a change in position of the control member relative to the second member, the amount of change in position being less than the selected amount of movement.

20 Claims, 4 Drawing Figures

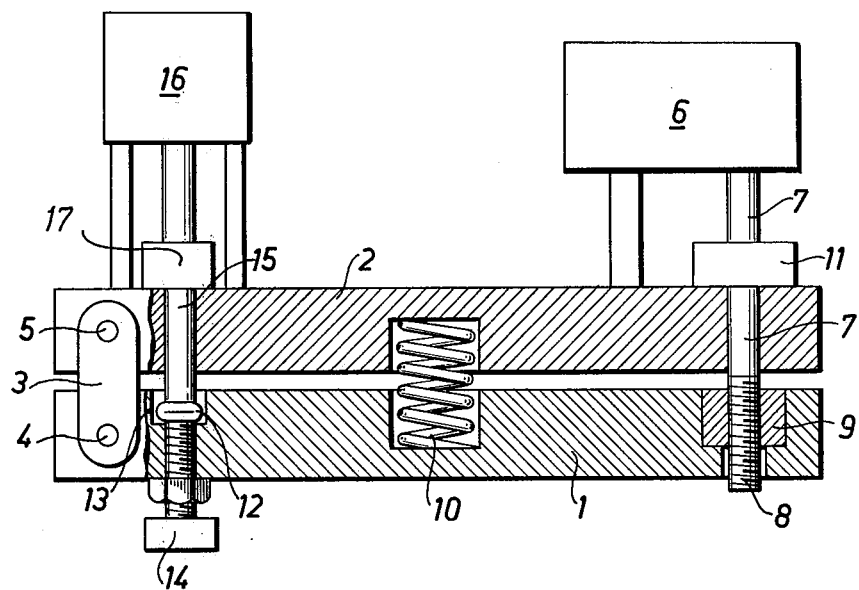
Fig.1
 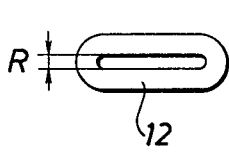 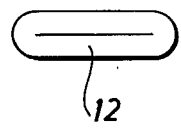
Fig.2A    Fig.2B    Fig.2C

CONTROL APPARATUS FOR CONTROLLING POSITIONING OF A CONTROL MEMBER

BACKGROUND OF THE INVENTION

The present invention relates to control apparatus and more particularly to apparatus for controlling the movement or positioning of a control member.

Many types of devices or articles must be accurately and finely controlled in a desired manner and to a desired degree in order to function properly. Often this desired control is accomplished by relative positioning of a control member in or with respect to the device or article which the control member is to control. That is, the positioning of the control member relative to the workpiece effects the desired control. Further in such arrangements, finely controlled positioning or adjustment of the control member will often effect control to a very fine degree.

For example, the size or opening of a flexible tube may be controlled by compressing, to different degrees, the tube to thereby control the amount of fluid flowing through such tube. This can be achieved by compressing the tube between a control member and a stationary support so that the distance between the end of the control member engaging the tube and the support for the tube is indicative of the size of the opening of the tube. Thus, by controlling to a very fine degree the positioning of the control member relative to the tube support, the size of the tube opening, and thus the amount of fluid flowing therethrough, may be controlled and adjusted to a correspondingly fine degree.

Accordingly, for these and other reasons, it is desirable to be able to finely control or adjust the positioning of a control member.

SUMMARY OF THE INVENTION

The control apparatus of the present invention for controlling the positioning of a control member comprises first and second members pivotally connected together to pivot about a point. A control member is supported on the first member and is disposed at a first distance from the pivot point. The control apparatus further includes coarse control means operatively associated with the control member for coarsely adjusting the position of the control member relative to the second member and fine control means for finely adjusting the position of the control member relative to the second member. The fine control means acts at an action point on one of the first and second members at a second distance to pivot the first and second members relative to each other about the pivot point. The action point is a second distance from the pivot point which is greater than the first distance so that a selected amount of movement of the action point results in adjustment of the position of the control member relative to the second member, the amount of change in position of the control member being less than the selected amount of movement.

In a preferred embodiment of the present invention, the second member comprises a support member which is adapted to support a workpiece which is to be controlled in a desired manner by adjustment of the position of the control element relative to the workpiece. In a still further preferred embodiment, the control member is supported on the first member for relative movement and the coarse control means is operative to move the control member relative to the first member to adjust the positioning of the control member relative to the second member.

According to a still further preferred feature of the present invention, biasing means, such as a spring, are provided between the first and second members to bias the members apart from one another in order that any play is always taken up in the same direction. Still further, according to another preferred feature of the present invention, the fine control means comprises a screw having a fine pitch which is appropriately supported by the first and second members so that relative movement of the first and second members is achieved by rotation of the screw.

These and further features of the present invention will be described in more detail with reference to the enclosed drawings which by way of example show a preferred embodiment of the control apparatus according to the present invention.

BRIEF DESCRIPTION OF THE DRAWINGS

FIG. 1 is a side elevational view, partly in section, of the control apparatus of the present invention; and FIGS. 2A, 2B and 2C show schematically three sections of a tube which is controlled by means of the control apparatus in accordance with the present invention.

DETAILED DESCRIPTION OF THE INVENTION

The arrangement in accordance with the present invention is intended primarily for use as a dosing valve in a dialysis system wherein it is often desirable to control the amount of fluid being introduced into the system. Such a dialysis system may for example be of the type which is described in U.S. application Ser. Nos. 841,898 now U.S. Pat. No. 4,158,034 and 841,899 since abandoned, both filed Oct. 13, 1977. While the present invention is so used in a dosage valve to control positioning of a control member to in turn control the size of the opening of a flexible tube, it is possible to control introduction of small amounts of a concentrate or introduction of substantially greater amounts of a sterilizing agent. Further, a rapid sucking of the latter agent may be combined with a very accurate dosing of the first-named agent. For those versed in the art it will be evident, however, that the control arrangement in accordance with the present invention can also be used for many other purposes.

The preferred embodiment of the present invention will now be described with reference to the Figures in which the control apparatus for adjusting the position of a control member is utilized to control the size of the opening of a hollow flexible tube. Referring to FIG. 1, there is shown a fixed support member 1 on which is mounted a pivot arm 2 via a steering arm 3. The steering arm 3 performs a pivotal movement about the axle 4 and the lever arm 2 a pivotal movement about the axle 5. At the same time the lever arm 2 naturally also performs a pivotal movement about the axle 4. The said pivotal movements are normally achieved by means of a motor 6 with the help of which a screw 7 is turned. This screw 7 is supported so that it is freely rotatable in the lever arm 2 and it passes with its thread 8 into a corresponding thread in a fixed bushing 9. This bushing 9 is arranged in the fixed support 1.

With the help of a spring 10, the lever arm 2 is pressed against a stop 11 on the screw 7. This causes any play in the movement of the members 1 and 2 always to be taken up in the same direction. This is very important, since the arrangement is used above all for fine control within a control range of such an order of magnitude that the maximum movement of a control member will be approximately 0.05–0.1 mm.

In the use of the present invention depicted in the drawings, the relative pivotal movement of the members 1 and 2 is used for the compression of a tube 12. The tube 12 is arranged in a tube holder 13 in fixed support member 1 and is adapted to be compressed by a control member 15 which is supported in lever arm 2. As shown in FIG. 1, a coarse control screw 14 is disposed beneath tube holder 13 on the side opposite from control member or plunger 15. As can be appreciated, by turning of control screw 14 in support 1, control screw 14 can control adjustment of the positioning of tube 12 relative to plunger 15. Further, plunger 15 is movable reciprocally within lever arm 2 by means of magnet 16 (such as for example a solenoid) which also controls the relative positioning of the plunger 15 with respect to the tube 12. Reference numeral 17 shows a stop on plunger 15 for defining the lower extent of movement of the plunger 15 relative to the lever arm 2. This coarse control through 14 and/or 16 may produce for example a direct change-over between the position of the tube 12 determined by the screw 7 and a wholly opened position. Alternatively, this coarse control may of course also take place in steps or continuously with a screw arrangement similar to the arrangement by which screw 7 provides fine control or adjustment.

FIG. 2A shows the shape of the tube 12 when the plunger 15 is in fully raised position. The tube is thus fully open and can be used for the transport of larger amounts of liquid. In FIG. 2B and 2C is shown how the tube can be controlled between a wholly closed position in FIG. 2C and an opened position in FIG. 2B by means of fine control screw 7 being adjusted to change the position of plunger 15 relative to the tube 12 supported in fixed support 1. Because screw 7 acts at a distance much farther away from the pivot axle 4 or 5 than the distance that plunger 15 is from the pivot axle 4 or 5, relative pivotal movement of the lever arm 2 and the fixed support 1 is geared down or reduced at the position of the plunger 15. Accordingly, rotation of screw 7 adjusts the position of the plunger 15 relative to the tube 12. For example, this control of the relative movement of the plunger 15 can be such that the maximum movement of the plunger will be approximately 0.05–0.1 mm. That is, if the control range for the amount of compression of the tube 12 is designated by letter R on FIG. 2B, this range R may vary between 0 and 0.5–0.1 mm.

Naturally, the invention is not limited solely to the embodiment described above but may be varied within the scope of the following claims. The lever arm 2 may, for example, be mounted so that it is supported directly in the support 1. Further modifications of the form and size of the details shown may also be made within certain limits, without thereby exceeding the scope of the invention.

What is claimed is:

1. Apparatus for adjusting the position of a control member relative to a hollow flexible tube, comprising:
    first and second members pivotally connected together to pivot about a pivot point;
    a control member mounted on said first member and disposed at a first distance from said pivot point;
    tube support means for supporting a hollow flexible tube on said second member relative to said control member so that said tube is adapted to be transversely compressed by said control member to vary the size of the opening of said tube and so that adjustment of the position of said control member relative to said tube provides a desired control of said tube by varying the distance between said control member and said tube support means;
    fine control means for finely adjusting the position of said control member relative to said second member, said fine control means acting at an action point on one of said first and second members to pivot said first and second members relative to each other about said pivot point, said action point being a second distance from said pivot point which is greater than said first distance such that a selected amount of movement of said action point results in adjustment of the position of said control member relative to said second member, the amount of change in position of said control member being less than said selected amount of movement; and
    coarse control means operatively associated with said control member for adjusting the position of said control member relative to said second member between a first position in which said fine control means is operative to finely adjust the position of said control member relative to said tube to thereby effect a change in control of said tube, and a second position in which said fine control means is inoperative to effect a change in control of said tube.

2. The apparatus of claim 1 wherein said coarse control means includes adjustment means for causing relative movement between said control member and said first member so as to vary the distance between said control member and said tube support means.

3. The apparatus of claim 2 wherein said coarse control means further includes means for moving said tube support means relative to said second member so as to vary the distance between said control member and said tube support means.

4. The apparatus of claim 1 wherein said fine control means comprises screw means threadably connected to said member on which said fine control means acts and means for rotating said screw means to move said first and second members relative to each other to adjust the position of said control member relative to said tube support means.

5. The apparatus of claim 4 wherein said means for rotating said screw means is supported on the member other than said member to which said screw means is connected.

6. The apparatus of claim 5 wherein said screw means is freely rotatable within said other member and further includes stop means on said screw means, and wherein said fine control means further includes biasing means for biasing said other member against said stop means.

7. The apparatus of claim 1 wherein said second member comprises a support member and a steering arm, said steering arm at one end being pivotally connected to said support member and at the other end being pivotally connected to said first member at said pivot point.

8. The apparatus of claim 1 wherein said coarse control means comprises adjustment means for causing relative movement between said control member and said first member.

9. The apparatus of claim 1 further including biasing means for biasing at least one of said first and second members for relative pivotal movement in a first direction so that any play in the movement of said members is always taken up in the same direction.

10. The apparatus of claim 9 wherein said biasing means comprises a spring operatively disposed between said first and second members to pivot said first and second members in a direction away from one another.

11. The apparatus of claim 1 wherein said fine control means includes means for incrementally adjusting the change in position of said control member in a range on the order of 0.05–0.1 mm.

12. Apparatus for controlling the positioning of a control element along a desired path including an operative portion in which said control element is operative to perform a control function comprising:
   a control element disposed in said path;
   coarse adjustment control means opeatively associated with said control element for coarsely controlling the positioning of of said control element along said path;
   an elongated fine adjustment control member operatively associated with said control element for finely controlling the positioning of said control element along said path;
   means pivotally mounting said elongated fine adjustment member for pivotal movement about a pivot point, said pivot point being located at first distance from said control element;
   fine adjustment control means acting on said elongated fine adjustment control member at an action point disposed a second distance from said pivot point which is greater than said first distance such that a selected amount of movement of said action point results in a change in position of said control element along said path, the amount of change in position of such control element being less than said selected amount of movement, said fine adjustment control means being operative to move said control element between first and second limits along said path;
   support means for supporting a hollow flexible tube adapted to be transversely compressed by said control element to vary the size of the opening of said tube, said support means being disposed in said path relative to said control element so that when said control element is positioned in said operative portion of said control path, movement of said elongated fine adjustment control member relative to said support means causes relative movement between said support means and said control element so as to vary the distance therebetween; and
   said coarse adjustment control means including moving means for moving said control element a distance greater than the distance between said first and second limits along said path so that said fine adjustment control means can be positioned to be inoperative to move said control element into said operative portion of said path.

13. The apparatus of claim 12 wherein said moving means is operative to move said control element in a direction away from said support means.

14. The apparatus of claim 12 wherein said support means comprises a support member and wherein said fine adjustment control means comprises screw means threadably connected to one of said members and means for rotating said screw means to move said elongated fine adjustment control member and said support member relative to each other to adjust the position of said control element relative to said support member.

15. The apparatus of claim 12 further including biasing means for biasing said elongated fine adjustment control member for pivotal movement in a first direction about said pivot point so that any play in the movement of said elongated fine adjustment control member is always taken up in the same direction.

16. Apparatus for adjusting the position of a control member relative to a workpiece, comprising:
   first and second members pivotally connected together to pivot about a pivot point;
   a control member having a longitudinal axis mounted on said first member and disposed at a first distance from said pivot point;
   support means for supporting a workpiece on said second member relative to said control member so that adjustment of the position of said control member relative to said workpiece provides a desired control of said workpiece by varying the distance between said control member and said support means;
   fine control means for finely adjusting the position of said control member relative to said second member, said fine control means acting at an action point on one of said first and second members to pivot said first and second members relative to each other about said pivot point, said action point being a second distance from said pivot point which is greater than said first distance such that a selected amount of movement of said action point results in adjustment of the position of said control member relative to said second member, the amount of change in position of said control member being less than said selected amount of movement; and
   coarse control means operatively associated with said control member for adjusting the position of said control member relative to said second member between a first position in which said fine control means is operative to finely adjust the position of said control member relative to said workpiece to thereby effect a change in control of said workpiece, and a second position in which said fine control means is inoperative to effect a change in control of said workpiece, said coarse control means including a magnet for moving said control member relative to said first member in a direction along said longitudinal axis of said control member.

17. Apparatus for adjusting the position of a control member relative to a workpiece, comprising:
   first and second members pivotally connected together to pivot about a pivot point;
   a control member mounted on said first member and disposed at a first distance from said pivot point;
   support means for supporting a workpiece on said second member relative to said control member so that adjustment of the position of said control member relative to said workpiece provides a desired control of said workpiece by varying the distance between said control member and said workpiece support means;
   fine control means for finely adjusting the position of said control member relative to said second member, said fine control means acting at an action point on one of said first and second members to pivot said first and second members relative to each other about said pivot point, said action point being a second distance from said pivot point which is greater than said first distance such that a selected amount of movement of said action point results in adjustment of the position of said control member relative to said second member, the amount of change in position of said control member being less than said selected amount of movement, said fine control means including screw means threadably connected to said member on which said fine control means acts and means for rotating said screw means to move said first and second members relative to each other to adjust the position of said control member relative to said second member; and coarse control means operatively associated with said control member for adjusting the position of said control member relative to said second member between a first position in which said fine control means is operative to finely adjust the position of said control member relative to said workpiece to thereby effect a change in control of said workpiece, and a second position in which said fine control means is inoperative to effect a change in control of said workpiece.

18. The apparatus of claim 17 wherein said means for rotating said screw means comprises a motor.

19. Apparatus for controlling the positioning of a control element along a desired path including an operative portion in which said control element is operative to perform a control function comprising:

a control element disposed in said path;

coarse adjustment control means operatively associated with said control element for coarsely controlling the positioning of said control element along said path;

an elongated fine adjustment control member operatively associated with said control element for finely controlling the positioning of said control element along said path;

means pivotally mounting said elongated fine adjustment member for pivotal movement about a pivot point, said pivot point being located at a first distance from said control element;

fine adjustment control means acting on said elongated fine adjustment control member at an action point disposed a second distance from said pivot point which is greater than said first distance such that a selected amount of movement of said action point results in a change in position of said control element along said path, the amount of change in position of such control element being less than said selected amount of movement, said fine adjustment control means being operative to move said control element between said first and second limits along said path, said fine adjustment control means including screw means threadably connected to said elongated fine adjustment control member and means for rotating said screw means to move said elongated fine adjustment control member to adjust the position of said control element along said path; and said coarse adjustment control means including moving means for moving said control element a distance greater than the distance between said first and second limits along said path so that said fine adjustment control means can be positioned to be inoperative to move said control element into said operative portion of said path.

20. The apparatus of claim 19 wherein said means for rotating said screw means comprises a motor.

* * * * *